(12) United States Patent
Hendrix

(10) Patent No.: US 6,524,787 B1
(45) Date of Patent: Feb. 25, 2003

(54) DIAGNOSTICS AND THERAPY BASED ON VASCULAR MIMICRY

(76) Inventor: Mary J. C. Hendrix, 7 Cherry La., NE., Iowa City, IA (US) 52240

( * ) Notice: Subject to any disclaimer, the term of this patent is extended or adjusted under 35 U.S.C. 154(b) by 0 days.

(21) Appl. No.: 09/649,585

(22) Filed: Aug. 29, 2000

Related U.S. Application Data

(60) Provisional application No. 60/152,490, filed on Aug. 30, 1999, and provisional application No. 60/151,406, filed on Aug. 30, 1999.

(51) Int. Cl.$^7$ .................................................. C12Q 1/00
(52) U.S. Cl. .............................. 435/4; 435/6; 435/325; 435/366; 435/375; 435/377; 435/397; 536/23.5
(58) Field of Search ................................ 435/6, 34, 91, 435/803, 366, 397, 91.2; 436/501, 813, 64; 536/27, 24.31, 24.33, 23.5

(56) References Cited

U.S. PATENT DOCUMENTS 4,981,783 A * 1/1991 Augenlicht ..................... 435/6
5,158,874 A * 10/1992 Kleinman ...................... 435/34

OTHER PUBLICATIONS

Folkman et al ,Sem. in Med. of Beth Israel Hospital, Boston, 1995, vol. 333 (26):175763–.*
Timar, J, et al, Pathol Oncol Res 2000; 6 (2): 83–86.*
Warren, BA, et al, Lab Invest 1966; 15 (2): 464–478.*
Konerding, MA, et al, Acta Anat 1989; 136: 27–33.*
Shubik, P, J Cancer Res Clin Oncol 1982; 103: 211–226.*
Folberg, R, et al, Opthalmol 1993; 100: 1389–1398.*
Hammersen, F, et al, Int J Microcirc: Clin Exp 1985; 4: 31–43.*
Warren, BA, J R Microscop Soc 1966; 86 (2): 177–187.*
Folberg, R, et al, Human Pathol 1982; 23 (11): 1298–1305.*
McDonald, DM, et al, Cancer Metastasis Rev 2000; 19 (1–2): 109–120.*
Arbiser, JL, Arch Dermatol 1998; 134 (8): 1027–1028.*
Barnhill, RL, et al, Arch Dermatol 1998; 134 (8): 991–994.*
Sharma, N, et al, Prostate 2002; 50 (3): 189–201.*
Maniotis, AJ, et al, Am J Pathol 1999; 155 (3): 739–752.*
Steeg, PS, Breast Cancer Res 2000; 2 (6): 396–399.*
Hendrix, MJ, et al, Breast Cancer Res 2000; 2 (6): 417–422.*
Folberg, R, et al, Am J Pathol 2000; 156 (2): 361–381.*
McDonald, DM, et al, Am J Pathol 2000; 156 (2): 383–388.*
Shubik, P, et al, Am J Pathol 2000; 156 (2): 736.*
Sood, AK, et al, Am J Pathol 2001; 158 (4): 1279–1288.*
Seftor, REB, et al, Cancer Res 2001; 61 (17): 6322–6327.*
Bissel, MJ, Am J Pathol 1999; 155 (3): 675–679.*
Hendrix, MJC, et al, Proc Natl Acad Sci USA 2001; 98 (14): 8018–8023.*
Hendrix, MJC, et al, Cancer Res 2002; 62 (3): 665–668.*
Barnhill, RL, et al, Lancet 1992; 339 (8799): 991–992.*
Hess, AR, et al, Cancer Res 2001; 61 (8): 3250–3255.*

* cited by examiner

Primary Examiner—Anthony C. Caputa
Assistant Examiner—Stephen L. Rawlings
(74) Attorney, Agent, or Firm—Scott A. Chambers

(57) ABSTRACT

The disclosed invention is directed to methods and apparatus for detection, prognostic diagnosis, treatment and prevention of cancer and other hyperproliferative disorders in humans and animals. More particularly, the present invention is directed to vascular mimicry factors that are expressed by tumor cells in various cancers and in diseased tissue and other disorders and methods and apparatus for detection and usage of such vascular mimicry factors. These claims are based on the recent discovery that aggressive, but not non-aggressive, tumor cells can "mimic" other cell types—in the expression of specific genes and in biological function.

2 Claims, 2 Drawing Sheets

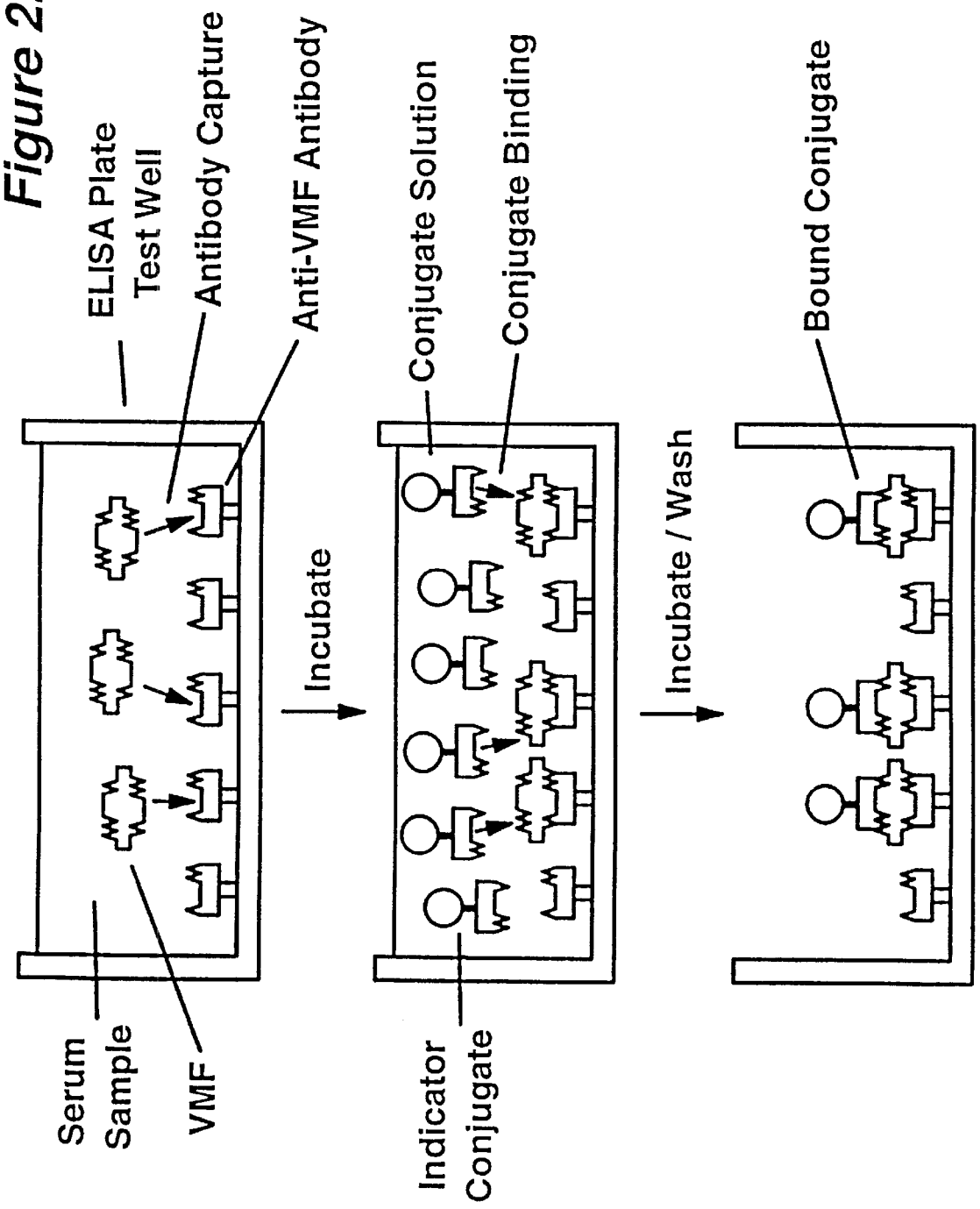

DIAGNOSTICS AND THERAPY BASED ON VASCULAR MIMICRY

This application claims priority to provisional application No. 60/152,490 with a filing date of Aug. 30, 1999 and also claims priority to provisional application No. 60/151,406 with a filing date of Aug. 30, 1999. These applications are hereby incorporated by reference into this application.

FIELD OF THE INVENTION

The present invention is directed to methods and apparatus for detection, prognostic diagnosis, treatment and prevention of cancer and other hyperproliferative disorders in humans and animals. More particularly, the present invention is directed to vascular mimicry factors that are characteristic of tumors, cancers, diseased tissue and other disorders and methods and apparatus for detection and usage of such vascular mimicry factors. Such vascular mimicry factors can be used in the detection, diagnosis, treatment and prevention of such cancers and disorders.

BACKGROUND OF THE INVENTION

It is well known that tumors exhibit various degrees of virulence (the tendency to proliferate, either at the primary tumor site or to remote, metastatic sites). While many tumors are slow growing and have little or no propensity to spread beyond the primary site, some tumors are highly aggressive. It is these rapidly growing, highly virulent tumors which are most dangerous.

A patient's prognosis is generally good if a tumor is discovered early enough and especially if the tumor is not particularly aggressive. For example, if a tumor is confined to the primary site, a physician will frequently design a course of treatment with the intent to cure the patient. However, the patient's prognosis is poor if a tumor is highly aggressive since the success rate for conventional treatment of such tumors is generally low. Thus, in such cases the physician is likely to design a course of treatment that is merely palliative.

Tumors that are growing aggressively require significant enrichment with various nutrients and oxygen to support their growth (which is very rapid relative to that of normal tissue growth). Therefore, such tumors tend to promote development of new vasculature, apparently in order to accommodate enhanced delivery of such nutrients and oxygen. It has been thought that this new vasculature was produced as a result of signaling agents produced by tumor cells, and that such agents would presumably serve to stimulate the growth of blood vessels into the tumor. It has furthermore been thought that the cells in this new vasculature were composed primarily of endothelial cells (i.e., cells normally found in and composing blood vessels) whose growth was signaled by various angiogenesis factors. Consequently, there have been significant recent efforts by several groups (such as those of Folkman, as illustrated, for example, in J. Folkman, "Seminars in Medicine of the Beth Israel Hospital, Boston, Clinical Applications of Research on Angiogenesis," *New Engl. J. Med* 333 (1995) 1757–1763) to use agents that inhibit such angiogenesis via application of various angiogenesis blocking agents (i.e., agents, such as endostatin and angiostatin, that inhibit the formation of normal vessels). Unfortunately, the effects of such angiogenesis blockers is not limited to tumor vasculature, but instead also inhibits blood vessel formation in normal tissue.

Hence, for improved ability to treat tumors, and especially aggressive, virulent tumors, it would be desirable to have agents that could selectively block formation of neovasculature formation in or around tumors without affecting normal vessel formation in healthy tissue.

SUMMARY OF THE INVENTION

The inventor has discovered that new vasculature in aggressive melanoma, prostate, glioblastoma and other tumors is produced from tumor cells (rather than from endothelial cells entering from outside the tumor), in a process termed "vascular mimicry." As a result inventor has found that certain individual genes and/or gene products, termed vascular mimicry factors or VMF, responsible for the formation of such vessels can now be identified using tissue culture and differential gene expression profiling methods, such as those disclosed in applicant's co-pending provisional application No. 60/151,406 with a filing date of Aug. 30, 1999. The present invention is directed to such VMF, and to methods and apparatus for identification, detection and usage of such VMF. The present invention is further directed to such VMF as the basis for development and manufacture of various diagnostic, prognostic and therapeutic products capable of selectively detecting, characterizing, treating or preventing such tumors.

The present invention has been made in view of the above circumstances and has as an object to identify VMF in various types of metastatic cells. A further object of the invention is to isolate and purify these VMF and to develop diagnostic tests for use in determining if VMF are present in a suspect cell line. A further object of the invention is to identify targets for anti-tumor agent development and manufacture. Further objectives include the creation of molecular vaccines and immunotherapy based on the VMFs. Additional objects and advantages of the invention will be set forth in part in the description which follows and in part will be obvious from the description, or may be learned by practice of the invention.

Thus, this invention contemplates a method of assaying for vascular mimicry factors comprising: isolating invasive tumor cells, isolating noninvasive cells, determining types and amounts of differentially expressed sequences using a microassay technique, and comparing the invasive and the noninvasive cell expressed sequence profile. It permits assaying for the presence of vascular mimicry factors using a serum antigen capture assay comprising: attaching to a solid phase an antibody elicited by injection of a vascular mimicry factor into an organism; incubation of the solid phase with media suspected of containing a vascular mimicry factor; incubation of the resulting product with a conjugated antibody to a vascular mimicry factor; determine the presence or absence of vascular mimicry factor. The invention permits a method of developing an immunogenic response in a patient comprising screening a suspect tumor in said patient for a vascular mimicry factor and raising antibodies to said vascular mimicry factors in said patient. When the vascular mimicry factor is placed in an expression vector, the product can be easily produced and used. Moreover, the inventor's discovery that VMFs are made by the actual tumor cell and not by endothelial tissue indicates that a method of assaying for the metastatic potential of a tumor cell can comprise growing suspect tumor cells in the absence of endothelial cells in a restrictive cellular matrix media and observing the production of vasculature-type structures.

BRIEF DESCRIPTION OF THE DRAWINGS

The present invention, together with its objects and advantages thereof, will be further understood by reference FIG. 2 illustrates examples of test methods for detection of differential gene expression factors for metastatic melanoma using a serum antigen capture assay.

DETAILED DESCRIPTION OF THE PRESENTLY PREFERRED EMBODIMENTS

Figure 1:
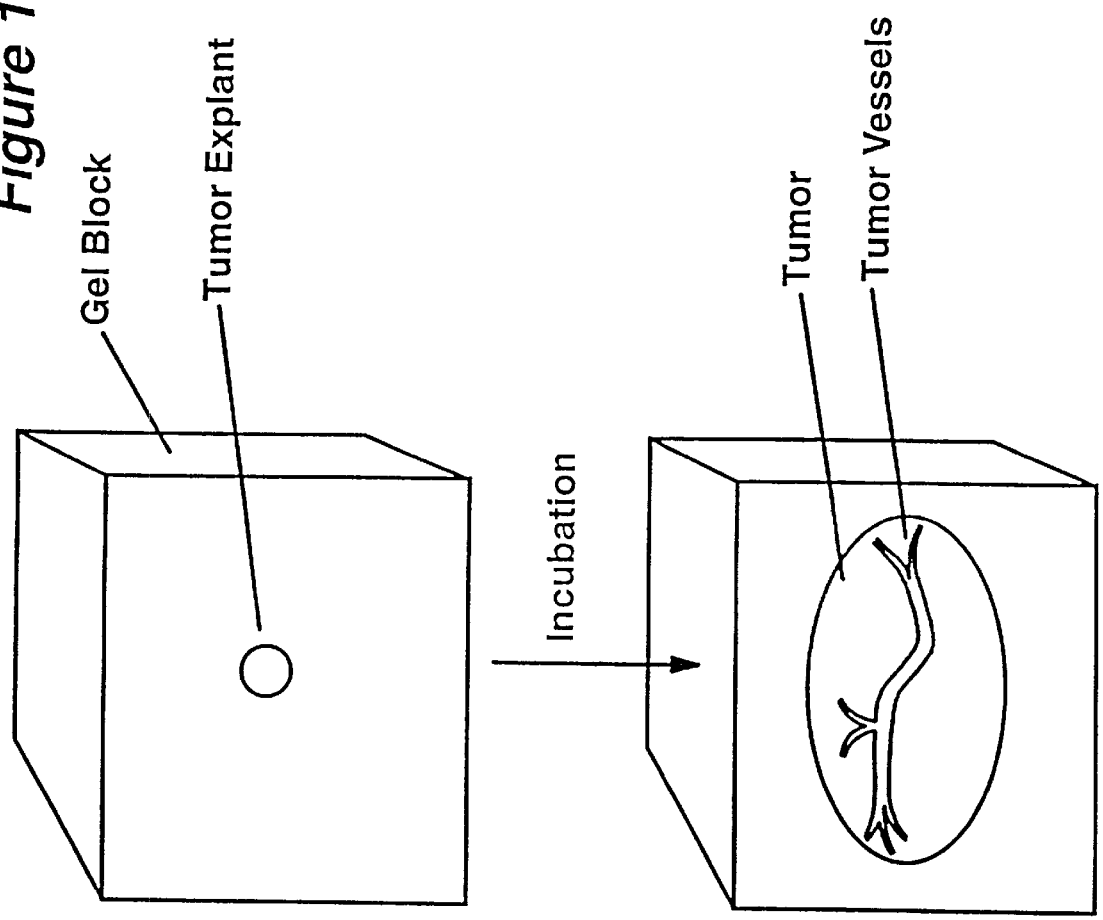
FIG. 1 illustrates example cell propagation methods and apparatus used for three-dimensional cell culture.

Recently, the inventor has discovered that the conventional paradigm of tumor vascularization is incorrect in aggressive tumors. In fact, she has discovered that the new vasculature in aggressive melanoma, prostate, glioblastoma and other tumors is produced from tumor cells (rather than from endothelial cells entering from outside the tumor). This process is termed vascular mimicry, and is controlled by genetic or molecular vascular mimicry factors (VMF). The primary implication of this finding is one embodiment of the present invention wherein certain gene and gene products responsible for the formation of such vessels in aggressive tumors (i.e., the VMF) can now be identified using tissue culture and differential gene expression profiling methods, such as those disclosed in co-pending provisional application No. 60/151,406 with a filing date of Aug. 30, 1999, which is incorporated herein by reference in its entirety. Further, in other embodiments of the present invention, such VMF can serve as the basis for various diagnostic, prognostic and therapeutic products capable of selectively detecting, characterizing, treating or preventing such tumors.

In general, the methods used to assay are well-known in the art in terms of buffer solutions, concentrations, hybridization conditions, and antibody antigen assay conditions. One preferred method would be that the cultured cells are collected and the RNA, or other nucleic acid, and the proteins are isolated. One preferred method of isolation is that described by Kahn et al., in *DNA Micro-Assay Technology: The Anticipated Impact on the Study of Human Disease*, Biochem. Biophys. Acta. 1423, 17–28 (1999), which is herein incorporated by reference.

Other general articles on methods that are helpful are found in teachings such as Hendrix, et al. *A Simple Quantitative Assay for Studying the Invasive Potential of High and Low Metastatic Variance*, Cancer Letters 38, 137–47 (1987); Hendrix et al., *Role of Intermediate Filaments in Migration Invasion in Metastasis*, Cancer Metastasis Review, 15, 507–25 (1996), which are herein incorporated by reference. Other techniques are found in publications such as Duggan et al., *Expression Profiling Using CDNA Micro-Assays*, Nature Genet. 21 10–14 (1999); Eisen et al., *Cluster Analysis and Displays of Genome-Wide Expression Patterns*, Proceedings of the National Academy of Science U.S.A., 95 14863–14868 (1998); Alizadeh et al., *Distinct Types of Diffuse Large B-cell Lymphoma Identified by Gene Expression Profiling*, Nature 403, 503–11 (2000); DeRisi et al., *Use of CDNA Micro-Array to Analyze Gene Expression Patterns in Human Cancer*, Nature Genet. 457–60 (1996); and Maniotis et al., *Vascular Channel Formation by Human Melanoma Cells In Vivo and In Vitro, Vasculogenic Mimicry*, American Journal of Pathology, 155, 739–752 (1999). These references are all incorporated by reference and they provide general methods to isolate DNAs, isolate protein and nucleic acids and to assay for those proteins and nucleic acids. In addition, general methods of analyzing this information as well as preparing the samples can be found in Bittner et al., Nature, 406, 536–40 (2000), which is incorporated herein by reference.

The nucleic acid or protein sequences that are used to create oliganucleotides or peptides can be determined by reference to any of the widely available public gene databases such as that of the National Center for Biotechnology Information (NCBI) which is a sequence database with the GenBank search and retrieval system. Similar public databases are those of the European Bioinformatics Institute within the European Molecular Biology Laboratories (EMBL) and the DNA Data Bank of Japan (DDBJ) These databases post their entries with reference numbers. For example, Neutral endopeptidase (CALLA, CD-10) has reference numbers NM000902; NM007289; NM007288; and NM007287. Other polymorphic variants of CALLA would also function in the assay. This is because a 100% sequence identity is not required. Generally speaking, the suspect tumor and the normal cell type will have the same or nearly the same sequence. Consequently, even if the probe or capture sequence differs from the target sequence, there will be little effect since the preferred mode of the assay uses the ratio to determine differential expression.

Cellular Basis of Vascular Mimicry

Cellular biology studies by the inventor have determined that aggressive tumors, such as aggressive melanoma, prostate, glioblastoma and other tumors, produce vessels that arise from a transformation of tumor cells into vascular-like structures. Differential gene expression studies by the inventor have shown that this transformation of neoplastic tissue (i.e., vascular mimicry) is controlled by a variety of differentially expressed genes and gene factors; these genetic or molecular factors are termed vascular mimicry factors (VMF). Thus, an embodiment of the present invention is directed to detection of over-expression of various VMF from tumor cells which can provide a way for detection or characterization of such cells. Similarly, in another embodiment of the present invention, control of VMF over-expression or activity in tumor cells, for example by blocking synthesis of VMF in such tumor cells, by competitively binding and passivating VWF receptors with inactive agents, or by stimulating an immune response to cells exhibiting such VMF over-expression, provides new and selective ways to suppress tumor genesis.

Candidates for such VMF include the proteins set forth in Tables 3–20 of 60/152,490. The Tables list the following gene/gene products: Neutral endopeptidase; Urokinase-type plasminogen activator; Transglutaminase (3' untranslated region); Corticosteroid 11-beta dehydrogenase 1; Carbamoyl phosphate synthetase 1; Tissue factor pathway inhibitor 2; Tissue factor pathway inhibitor; Serum amyloid A protein precursor; Nicotinamide N-methyltransferase; Carbonic anhydrase 1; Cystathioase-gamma; Mitochondrial transfunctional enzyme; Sialytransferase SthM; Sialytransferase 1; Sialytransferase 8; Gal-beta (1-3/1/4) GlcNAc; Sterol 27-hydroxylase; Alpha 2-macroglobulin; Ribophorin II; Glutathione S-transferase; GST Theta 2; GST Zeta 1; NADPH(P): menadione oxireductase; Dihydropyrimidine dehydrogenase; Phosphodiesterase 4B; KIAA0520 (Adenyl cyclase type IX); L-3-phosphoserine-phosphatase homologue; Plasminogen activator inhibitor 1; Bleomycin hydrolase; KIAA0089 (Glycerol-phosphate dehydrogenase); Long chain fatty acid acyl-coA ligase; Ribonuclease inhibitor; Pyrroline-5-carboxylate dehydrogenase (long form); Ribose 5-phosphate isomerase; D-beta-hydroxybutyrate DH; and Phosphoenolpyruvate carboxylase; Ly-GDI (Lymphoid-specific GDP dissociation inhibitor); RP3; ADP-ribosylation factor; ARF-4; GEM; and G protein coupled receptor LCRI; GTP Binding Proteins/GTPases; PAX-8, Basonuclin; FER-1; Transcription elongation factor B-elongin A; c-jun proto-oncogene (AP-1); Staf 50; Neuronal apoptosis inhibitory protein; Friend Leukemia virus integration 1 (Fli-1); HC enhancer-binding protein MAD3; Drosophila Msh homeo box homolog 1; TNF type 2 receptor associated protein (TRAP3); Nuclear factor RIP140; Histone H2A X; Drl-associated corepressor (DRAP1); Anti-silencing protein 1; MADS-box transcription enhancer factor 2, polypeptide C (MEF 2C); Binding regulatory factor; Human 100 kDA coactivator mRNA; IPW (imprinted Prader-Willi region); Inhibitor of DNA binding 2; CRM1; J Kappa recombination signal binding protein; and AEBPI; Protein Processing Factors; KIAA0057 gene; DNAJ protein homologue 1 (hsp 40); Translation initiation factor eIF-2-alpha; SEC 14-like protein; Synuclein alpha; ATP-binding protein; Translational inhibitor protein, 14.5 kDa; PIG F; PIG 11; PIG 7; YPT3 (rab 11); Syntaxin 5A; Proxisome biogensis disorder protein 1 (PEX1); and Calumein mRNA; Glycoproteins and Receptors Urokinase receptor (uPAR); Membrane glycoprotein M6b; Activated leukocyte cell adhesion molecule (ALCAM); Neuritin; Neural cell adhesion molecule (CALL), Proteolipid protein; Class II MHC antigen (M alpha chain); Clathrin coat assembly protein AP50 (KIAA0190); Retinoic acid receptor, β2; SDF5; CD59 antigen (Protectin); Duffy blood group (IL-8 receptor); CD9 antigen; N-acetyl-beta-D-glucosaminide; Human putative copper uptake protein (HCTR2); Dystroglycan (DAG 1); and Polycystic kidney disease protein 1; RNA Processing; Arginine-rich nuclear protein; and Splicing factor; Translational Control Factors; Ribosomal protein L23; Ribosomal protein L4; Ribosomal protein S17; Initiation Factor-2, mitochondrial; and Translation initiation factor 4A; Growth Factor Receptor Kinases and Signal Transduction Factors; TIE-1 (receptor kinase); ECK (epithelial cell kinase); Hematopoetic-lineage cell-specific protein (HS1; p50); Myosin light chain kinase; Receptor protein tyrosine kinase; Phophoinositide 3-kinase (PI 3-kinase); Serine/threonine protein kinase SGK; Protein phosphatase 6; Dyrk4 (protein kinase); PCTAIRE protein kinase 3; Erythropoietin receptor; and Protein-tyrosine phosphatase receptor, type f; Extracellular Matrix Proteins; Fibrillin-1; Collagen VI (alpha 3), Collagen I (alpha2); Fibronectin 1; Lumican; Extracellular matrix protein 1; and Collagen binding protein 2; Tumor Associated Antigens; L6 tumor associated antigen; S100A; S100P; S100 protein-beta chain; p37NB; Apolipoprotein D; Apolipoprotein C-II; MART-1; Melanoma associated tyrosinase; MAGE-10; PRAME; and Presentilin 2 (alzheimer); Cell Cycle Factors; RACHI, Cyclin-selective ubiquitin carrier protein; Peripheral myelin protein 22; and NEDD-44 (ubiquitin) protein ligase); DNA Repair Factors; KIAA0086 (yeast SNM1 protein); and PMS4; Cytoskeleton/Binding Proteins; Keratin type II cytoskeletal 7; Keratin-8; Plakophilin 2a/b; Smoothelin; Lymphocyte specific protein LSP-1 (pp52); Villin 2 (Ezrin); Neutral calponin; Thyroid autoantigen (TABP); Myosin heavy polypeptide 9 (non-muscle); Flightless I (Drosophila) homolog; Tubulin, alpha 4 chain; and Crystallin alpha-B; Growth Factors and Related Proteins; Connective tissue growth factor; VEGF-related protein (VRP); Inhibitors of apoptsis (IAP), homolog C; Latent TGF beta-binding protein 2; Semaphorin/collapsin (CD100); Insulin-like growth factor binding protein-1; Insulin induced growth response protein (human INSIG 1); Insulin receptor substrate-1; Heparin-binding EGF-like growth factor; Insulin-like growth factor binding protein-3; and Insulin-like growth factor 1 receptor; Ion Channel and Pump Factors; TWIK-1; Beta cell type calcium channel alpha 1; Cytochrome bc-1 complex core protein II; ATPase H+ transporting lysosomal 42KD; Annexin VII (synexin); and Kidney and cardiac voltage dependent K+ channel (KvLQT1); Modulators; GABA(A) epsilon subunit; Transferrin; Multidrug resistance protein-1; Canalicular MRP; MRP5; Small proline rich protein; Hermansky-Pudlak syndrome; and Metallothionein-1G (MT1); Cytokines and Related Proteins; Leukemia inhibitory factor (LIF); Interleukin-15 receptor alpha chain, Interleukin-16; and IL-1 receptor accessory protein; Oncogenes and Tumor Suppressor Genes; RIG (regulated in glioma); ETS-2 human, v-ets proto oncogene; ETS-related protein ERM; EXTR2 (EXT-related gene); Retinoblastoma-like 1 (p107); v-myc; Immunoglobulin Mu; and Hematopoietic specific early response protein (A1). Other candidates include sequences differentially expressed in the vascularized tumor compared to normal cells or non-vascularized tumors.

The figures illustrate not only a preferred method of cell culture, but also methods of assay using serum of tissue culture supernate. FIG. 1 illustrates example cell propagation methods and apparatus used for three-dimensional cell culture; As shown in the figure, the suspect tumor is placed within the cell culture media and then is permitted to grow. Cell cultures producing VMFs show a greater propensity to develop vasculature in culture. FIG. 2 illustrates examples of test methods for detection of differential gene expression factors for metastatic melanoma using a serum antigen capture assay. This form of sandwich assay permits the use of complex media such as blood serum and to assay in the presence of contaminating material.

Diagnostic Test Factor Development and Use

The discovery that new vasculature in aggressive tumors is produced as a result of vascular mimicry under the control of various VMF agents allows changes and such VMF agents to be used as the basis for various new diagnostic, prognostic and therapeutic products capable of selectively detecting, characterizing, treating or preventing such tumors. More specifically, the identification and use of various differentially expressed antigens and related genes and gene products associated with transformation of neoplastic (i.e., tumor) cells into vessels, based on the tissue culture and differential gene expression profiling methods described in applicant's co-pending provisional application no. 60/151,406 with a filing date of Aug. 30, 1999, provides such basis.

More specifically, the inventor has found that this special transformation of neoplastic cells, which is distinctly different than that of the conventional model of neovascularization based on localized promotion of endothelial cell growth into tumors, allows specific differential gene expression profiles of such vascular mimicry transformation to be obtained. It further allows for such profiles to be used in the development and manufacture of effective diagnostic, prognostic, and therapeutic products for various metastatic and non-metastatic disorders such as various skin cancers, including melanoma; breast cancer; prostate cancer; renal cancer; liver cancer; lung cancer, brain cancer and other head and neck cancers, including glioblastomas; lymphomas, and leukemias. Such products will not suffer from the lack of specificity that plagues anti-angiogenesis-based approaches, which, as discussed herein, are not based upon and do not address the specific vascular transformations and control factors (i.e., VMF) that are substantially critical to and characteristic of tumorogenesis, proliferation, and metastasis.

Further, such differential gene expression profiles and the associated identified VMF agents indicated by such profiles can be used for the manufacture of a variety of new or improved, simple test kits or other related apparatus for analysis of primary tumor explants and suspect tissue samples, as well as blood, blood products, or other bodily fluids, including urine and saliva. Such simple test kits or other related apparatus would provide similar but substantially improved functionality, for example, to that of standard direct histologic and histochemical tests, as well as to that of indirect tests, such as the prostate specific antigen test ("PSA") for prostate cancer. Such tests would be useful for very selective and sensitive direct or indirect diagnosis of the presence of, and for characterization of the virulence of or virulent propensity of, various cancers.

In an example of the present invention, such a profile of differentially expressed genes and related gene factors, including VMF agents, in aggressive tumors can be identified by growing a primary tumor explant or other tumor cell line in a special tissue culture chamber consisting of a three-dimensional culture system in a soft gel (i.e., composed of collagen, such as MATRIGEL). Such a gel provides a more restrictive cellular matrix for growth of the tumor and provides a more naturally environment for the tissue growth. Consequently, a restrictive cellular matrix growth medium is defined as one that provides a more natural three dimensional structure for artificial cell growth. This is illustrated in FIG. 1. This culturing process induces aggressive tumor cells to produce a tumor that is substantially similar to a natural tumor grown in vivo. The nascent aggressive tumor will tend to differentiate differently relative to that of a non-aggressive tumor. One such difference is the production of vessels by or from tumor cells. Thus, a significant advantage of this culturing process is that tumor tissue undergoing active vascular mimicry, and hence exhibiting expressed VMF, can be readily obtained. Samples of these tissues can thus be analyzed for differential gene expression relative to non-transformed tissue (i.e., tissue not exhibiting vascular mimicry) via common mass-screening techniques (such as microarray analysis or differential display analysis) so as to determine the differentially expressed factors (i.e., various VMF agents and factors) underlying such vascular mimicry. Alternately, samples of vasculature from natural tumors can be analyzed for differential gene expression.

Various VMF agents and other related factors identified by such analysis thereby serve as the basis for development and manufacture of the desired diagnostic, prognostic or therapeutic agents.

General examples of representative methods and uses of such factors in the present invention are provided in the following examples. These examples are merely for illustrative purposes and are not intended to limit the present invention.

EXAMPLE 1

Serum Antigen Capture Assay

Many expressed gene products in cancer cells are "shed" from the cancerous cells, and can often be found in trace levels within serum. Differential gene expression of various vasculature mimicry factors, of the present invention, by tumor cells can result in the appearance of shed VMF in serum and other bodily fluids. Thus, cancer and other neoplastic disease can be diagnosed using serum obtained via venipuncture. Any of a range of standard tests can be used on such serum samples as a way of quantifying the presence and/or the amount of VMF in such samples. For example, an Enzyme Linked Immunosorbent Assay (ELISA) antigen binding plate, such as that illustrated in FIG. 2, that is coated with anti-VMF antibody provides a simple way of detecting VMF. The solid phase for such a test can also consist of, among numerous possibilities, an organic or inorganic bead, nitrocellulose paper, coated tube, or Staphylococcus aureus proteins, for example, wherein covalent or non-covalent bonds are used to bind the primary antibody to the solid phase. Serial dilution of the serum sample into wells, followed by incubation under standard conditions, allows the shed VMF antigen in the serum of cancer patients to be "captured" by the bound antibody. This test plate is the incubated with a secondary anti-VMF antibody/indicator conjugate, washed, and the quantity of bound conjugate quantified via conventional techniques (for example, based on fluorescence of the indicator). In this way, the conjugate (for example, anti-VMF antibody complexed to fluorescein) serves as an indicator of VMF by binding only to VMF that has become bound to the test plate and remaining after washing only where so bound. The residual fluorescein component of the conjugate thereby provides a colorimetric or photometric way of detecting the presence of VMF on the plate, and thereby quantifying the presence and/or amount of VMF in the serum. Such a plate can be read visually or using an automated ELISA reader. The level of free serum VMF is then compared to that of normal patients and serum from cancer patients without aggressive tumors. In this example, elevated levels of free VMF indicate that the patient has aggressive neoplastic disease.

EXAMPLE 2

Combined Functional Enzymatic Assay

Through the use of differential gene expression profiling of the present invention, the inventor has shown that certain over-expressed or under-expressed antigens associated with aggressive tumors are functional enzymes. Some over-expressed functional enzymes in aggressive tumors can participate in vascular mimicry (i.e., they will function as VMF agents). Indirect measurement of the level of VMF in a sample, such as in a serum sample, using a functional assay (an assay responsive to the presence and function of VMF) will be many times more sensitive than a mass-based detection approach for quantification of VMF, such as that described in FIG. 2. Thus, a simple functional assay can be used to detect over-expression of VMF by tumor cells with very high sensitivity. However, the specificity of such an assay will be negatively impacted unless specific test conditions are used to assure that other functional enzymes, such as normal proteases, that might be present in the sample cannot produce spurious results. Thus, to avoid false positives from the presence of such other functional enzymes in a particular sample, a hybrid immunoassay/functional assay can be used to analyze the sample. For example, anti-VMF antibodies bound to a solid phase (such as an ELISA plate, tube, nitrocellulose paper, or bead, or other suitable material) can be used to provide selective capture and retention of VMF present in a sample, such as a patient's serum. Incubation of such serum with such solid phase, followed by washing to remove undesired serum components, leaves substantially only bound VMF on the solid phase. Subsequent application of a functional assay that is responsive to one or more VMF components to this solid phase allows the amount of bound VMF to be determined based on VMF function.

The activity of VMF, or of any other enzymatically active gene product related to vascular mimicry, can be determined using this example of the present invention. Specifically, the high specificity of the first step (based on immunoassay)

allows isolation of only the desired expressed enzymatic factor. Coupling this step with the extreme sensitivity of the functional assay step facilitates ultra-selective, ultra-sensitive determination of VMF enzyme expression levels in extremely complex samples, such as human serum. Thus, indirect detection or diagnosis of aggressive tumors based on serum levels of VMF or other functional enzymes related to vascular mimicry, singly or in conjunction with other functional enzymes or other gene expression factors associated with such disease, is made possible and practical by this example of the present invention.

EXAMPLE 3

Specific Antibody Test for Differentially Expressed Gene Products

Another example of the present invention is directed to VMF and antibodies to such VMF and related factors. More specifically, patients with cancer may exhibit one or more differentially expressed tumor markers which can induce a serum antibody response by the immune system. For example, patients with pre-neoplastic liver disease may exhibit an antibody to certain tumor markers in their serum well before the onset of true neoplasia. Therefore, metastases, primary tumors, or various other neoplastic or pre-neoplastic lesions associated with aggressive tumors can be detected or diagnosed via ELISA or immunoassay methods responsive to antibodies induced by such tumors.

For example, shedding of excess VMF into the vasculature compartment by aggressive tumor cells can induce an immune response to such VMF. Thus, the potential for or presence of aggressive tumor behavior can be detected by evaluating serum antibody levels for the appropriate target, such as anti-VMF antibody. For example, an antigen capture ELISA test, similar to that described in FIG. 1, wherein purified VMF is bound to the solid phase, allows the level of anti-VMF antibodies in samples, such as serum, to be determined. Comparison of serum antibody levels in patients suspected of harboring aggressive tumors is compared to normal patients and patients with non-aggressive tumors in order to calibrate assay response. Thus, indirect detection or diagnosis of aggressive tumors based on serum levels of anti-VMF or other anti-tumor antibody markers, singly or in conjunction with other anti-tumor antibody markers or other gene expression factors associated with such disease, is made possible and practical by this example of the present invention.

First Embodiment

One embodiment of the present invention is directed to methods and apparatus for diagnostic testing of humans or animals based on one or more genetic or molecular vascular mimicry factors identified by differential gene expression profiling, wherein specific antigens, genes, gene products or other factors identified from tumor cells exhibiting vascular mimicry are used as or for a diagnostic profile. Preferably, such diagnostic tests are used to detect the presence of transformed cells as well as for prognostic indication of the propensity of suspect cells to become virulent or aggressive. It is further preferred that such profiles be conducted using primary tumor explants from specific patients. Alternately, such profiles can be conducted by pooling results from multiple patients so as to develop a profile based on conserved factors common among multiple patients. This also could be the basis for building a database. Such respective profiles can be used in the manufacture of a maximally-selective test for a specific patient, or alternately as a substantially universal test for multiple patients, including patients unrelated to the tested population.

As a further preferred embodiment, such testing may be conducted directly upon samples of suspect human or animal tissues, or, as taught herein, by indirect testing based on various differentially-expressed vascular mimicry factors, or the indicators of such factors that are shed by such cancerous cells into bodily fluids of humans or animals, including, but not limited to, blood, blood products, or other bodily fluids, including urine and saliva. Applicable differential gene expression factors, or indicators of such factors, appropriate for such indirect testing include but are not limited to: various nucleic acids, including DNA, RNA, and other oligonucleotides and nucleic acid sequences; various amino acids, peptides, proteins and glycoproteins; various antigens and antibodies; various carbohydrates; various lipids, fatty acids, and lipopolysaccharides; along with various cellular function and transduction control elements, such as enzymes and inhibitors.

Anti-Tumor Agent Development and Manufacture

In addition to the aforementioned diagnostic and prognostic applications, the inventor has found that the differential gene expression profiles for vessel mimicry of the present invention can be used for the development and manufacture of various anti-tumoral agents. Such agents can be used to control, eradicate, or prevent various growths, including metastatic and non-metastatic tumors, pre-neoplastic lesions, benign hyperplasias, and other hyperproliferative growths. Specifically, the differential gene expression profiles can be used to develop and manufacture specific therapeutic or immunotherapeutic agents that, upon administration to a human or animal, serve to stimulate an immune response in such human or animal to specific growths, or certain cells in such growth, responsible for or involved in vessel mimicry. For example, an immunotherapeutic agent (or medicament) based on the differential gene expression profile for cells involved in vessel mimicry can be used to attack such cells where they pre-exist, or to prevent nascent proliferation of such cells, and can thereby provide a potent and highly selective anti-tumoral effect.

Such immunotherapeutic agents can be produced based on specific differential gene expression profiles obtained on a patient-by-patient basis, for example by profiling primary tumor or metastatic tumor explants, thereby producing agents specifically targeted to cells from or related to such explants. Such agents would afford maximum specificity for a particular target, such as vessel mimicry in metastatic melanoma in a particular patient.

Alternately, such agents can be produced based on conserved differential gene expression profiles (i.e., expression factors that are common among many or all patients having a specific cancer or other growth), for example by profiling primary tumor or metastatic tumor explants from multiple human or animal patients having a certain cancer or other growth, and then producing agents targeted to the common factors in such a set of profiles. Such agents would afford improved universality in the applicability of such agents to a particular target in multiple patients, including patients unrelated to the profiled patient population. Furthermore, it would be possible to use such agents as a prophylactic vaccine to prevent nascent vessel mimicry in unaffected patients.

Alternately, such agents can be produced based on highly conserved differential gene expression profiles (i.e., expression factors that are common among many or all patients having a variety of different cancers or other growths), for example by profiling primary tumor or metastatic tumor explants from multiple human or animal patients suffering from a variety of different cancers, and then producing agents targeted to the common factors in such a set of profiles. Such agents would afford further improved universality in the applicability of such agents to several or more particular targets in multiple patients, including patients unrelated to the profiled patient population. Furthermore, it would be possible to use such agents as a prophylactic vaccine to prevent nascent vessel mimicry in any of a multitude of targets in unaffected patients. For example, such agents might be used in a prophylactic fashion to prevent nascent vessel mimicry for a range of, or perhaps all, cancerous diseases.

Such agents could be used in close conjunction with a diagnostic assay, such as those described herein; if the diagnostic assay indicated the presence of a tumor or other growth with a high propensity for virulence, the appropriate agent could then be administered immediately so as to arrest progression of the disease or to completely clear the disease from the patient.

Such agents could thereby be used to control, eradicate or prevent various growths, including metastatic and non-metastatic tumors, pre-neoplastic lesions, benign hyperplasias, and other hyperproliferative growths, including those of various skin cancers, including melanoma; breast cancer; prostate cancer; renal cancer; liver cancer; lung cancer; brain cancer and other head and neck cancers, including glioblastomas; lymphomas; and leukemias. For example, such agents could be used to prevent progression of disease beyond a primary site as well as for treating or even preventing the formation of the primary tumor.

Illustrative examples of such methods and uses are provided in the following examples. These examples are merely for illustrative purposes and are not intended to limit the present invention.

EXAMPLE 4

Molecular Vaccine/Immunotherapy

Certain tumors may express antigenic agents at levels that are significantly enhanced above those found in normal cells. However, as in the case of warts caused by papilloma virus, these expressed tumor antigens may go undetected by the immune system. Thus, the immune system may be unable to recognize such a tumor. In some cases an invasive procedure affecting such a tumor (such as a biopsy) may unmask the previously shielded tumor antigen, resulting in an immune response which leads to dramatic cure of the cancer.

This unmasking can be achieved using certain differentially expressed gene factors, such as VNF of the present invention. For example, potent anti-tumoral immunotherapeutic agents may be produced by cloning the reading frame responsible for synthesis of a VMF agent into a eucaryotic expression vector or plasmid; alternatively, this genetic code may be cloned into a suitable viral vector (such as herpes virus, pox, retrovirus, and adenovirus, among others). For example, a gene sequence coding for one or more VMF agents or factors can be inserted into an appropriate expression vector (such as a plasmid, cosmid, or virus). Injection of this expression vector into a patient will result in infection of the patient by the vector and subsequent production of the encoded protein. The resulting over-expression of VMF will thereby induce an immune response to cells exhibiting over-expression of VMF, such as those in the tumor. Such induced immune response can thereby be utilized to prevent growth of aggressive primary tumors or to reduce or resolve existing tumors.

EXAMPLE 5

Gene Product Vaccine/Immunotherapy.

In another example of the present invention, VMF antigen, or any other antigenic material or factor useful for in vitro production of an antigenic material, that is over-expressed in aggressive tumors can be used as a vaccine to prevent primary tumors or their prevent metastasis. Such agents can be identified via differential gene expression profiling of the present invention. For example, VMF antigen can be efficiently produced in vitro using recombinant DNA methods. Such synthetic VMF antigen can be used directly to stimulate an immunotherapeutic response, such as illustrated in Example 4. Further, the antigenicity of the synthetic VMF antigen can be further enhanced by chemically complexing it with a molecule that appears foreign to the host immune system (i.e., to a hapten). For example, keyhole limpet hemocyanin or an animal immunoglobulin can be chemically attached to the target antigen (such as synthetic VMF antigen) to form a haptenated antigen; such haptenated antigen can be used directly to stimulate an immunotherapeutic response, such as illustrated in Example 4. Efficacy of this haptenated antigen can be further enhanced by mixing it with an agent that non-specifically enhances immune response (such as an adjuvant like aluminum hydroxide). The resulting immune response to exposure of the patient to any of these agents can thereby be utilized to prevent growth of aggressive primary tumors or the production of metastases, or to reduce or resolve existing tumors.

EXAMPLE 6

Conventional Drug Targets

Since some differentially expressed gene products, like some VMF agents, are enzymatically active, drugs that can inhibit the action of or block the biosynthesis of such enzymes can be easily found using standard mass screening techniques. Differential gene expression profiles for such products or other actors of the present invention provide crucial guidance for efficient discovery of such VMF agents and VMF agent precursors, along with the drugs useful for inhibition of such function or of other cellular processes involved in tumorogenesis.

A combined functional enzymatic assay, such as that described in Example 2, can be used, with slight modification, for mass screening of potential drug candidates useful for enzyme inhibition. For example, an identified target enzyme, such as VMF, can be immunosorbed onto a solid surface using the procedures described in Example 2. Drug candidates can then be evaluated on their ability to inhibit activity of the enzyme.

Alternately, drug candidates useful for inhibition of specific synthetic pathways identified by differential gene expression can be screened in similar fashion. For example, agents capable of inhibiting synthesis of various VMF agents can be screened based on knowledge of these agents and their synthetic pathways.

Alternately, drug candidates useful for inhibition of the function of specific VMF agents, for example by competitive binding with VMF receptors or by passivating the VMF agent itself, can be screened in similar fashion.

The resulting drug candidates can then be tested for efficacy in prevention of growth of aggressive primary tumors or the production of metastases, or for reduction or resolution of existing tumors or metastases. Candidates exhibiting positive tumorocidal properties, for example arresting of aggressive tumor growth, can then be used to treat patients suffering from such tumors.

Second Embodiment

In another embodiment of the present invention, differential gene expression profiles for vessel mimicry, for example those involved or expressed in various metastatic and non-metastatic tumors, pre-neoplastic lesions, benign hyperplasias, and other hyperproliferative growths, including those of melanoma, various skin cancers, breast cancer, prostate cancer, renal cancer, liver cancer, lung cancer, brain cancer and other head and neck cancers, lymphomas and leukemias are used for the development and manufacture of various immunotherapeutic agents useful for control, eradication or prevention of such growths. Preferably, such immunotherapeutic agents are based on specific differential gene expression profiles for vessel mimicry that are obtained on a patient-by-patient basis. Alternately, such immunotherapeutic agents are based on conserved differential gene expression profiles for vessel mimicry that are common among multiple patients. Alternately, such immunotherapeutic agents are based on highly conserved differential gene expression profiles for vessel mimicry that are common among multiple patients having, in ensemble, two or more different cancers or other growths.

General methods of analyzing this information as well as preparing the samples for microassay can be found in Bittner et al., Nature, 406, 536–40 (2000), which is incorporated herein by reference. The nucleic acid sequences that may be necessary to create oligonucleotides or to make small fragments can be determined by reference to any of the widely available gene databases such as that of NCI or EMBL.

This invention permits the method of detecting tumor virulence or metastatic potential as well as diagnosing invasiveness and gives a prognostic indicator of an individual's ability to respond to cancer therapy. The gene expression profiles can be most easily used by comparing a number of individual factors, the differential expression of a number of differential factors, to determine whether or not the suspect cells are invasive or not.

In addition, amplification methods that are known in the art such as those using the Polymerase Chain Reaction can be used to amplify the sequences to increase the signal strength as long as the amplification methods have the ability to qualify the initial or end result of the amplification. While the exact amount of differential expression is not as important as the evidence of differential expression, it is preferable that the differential expression be within 50% of that shown and more preferably within 25% of that set forth in the application and even more preferable that it be within 15% and more preferable that it be within 5% or higher of the differential expression data for normal or noninvasive cells.

However, it should be understood that individual factors may not be elevated or may not be differentially expressed in any particular type of tumor cell and for that reason it is expected that an individual will look for large numbers of these differential expressions, and the greater the similarity with metastasizing cells the greater the likelihood that the unknown cell will be a highly metastatic cell.

Expression markers are markers that indicate that a certain sequence or factor (as set forth in the tables) has been expressed and can include the RNA, cDNA from the RNA, or protein that arises from translation of the RNA. Methods of assay can include hybridization, antibody assays, assays for protein activities of the factors in the tables, or direct isolation and detection of a protein. Known level of expression can include those from deposited cells as well as normal cells or comparisons with the amounts provided in the tables such as those set forth in Ser. No. 60/152,490 and 60/151,406.

This description has been offered for illustrative purposes only and is not intended to limit the scope of invention of this application. It will be apparent to those skilled in the art that numerous modifications may be made therein without departing from the scope of the invention.

I claim:

1. A method for determining the propensity of a melanoma to become virulent or aggressive, wherein said method comprises growing a primary melanoma tumor explant or tumor cells derived therefrom in the absence of endothelial cells in a three-dimensional culture system composed of a soft gel matrix and determining whether or not said explant or cells derived therefrom in the absence of endothelial cells form vasculature in the three-dimensional culture system, thereby determining said melanoma to either have the propensity to become virulent or aggressive if said vasculature forms or not to have said propensity if said vasculature does not form.

2. A method for developing a gene expression profile that differentiates a melanoma having the propensity to become virulent or aggressive and a melanoma not having said propensity, wherein said method comprises:

(a) determining the levels of expression of genes in a primary melanoma tumor explant or tumor cells derived therefrom, (c) determining whether or not said explant or tumor cells derived therefrom form vasculature in a three-dimensional culture system composed of a soft gel matrix in the absence of endothelial cells, and (d) identifying one or more of said genes and the levels of expression of which correlate with the ability or inability of said explant or tumor cells derived therefrom to form vasculature in the culture system in the absence of endothelial cells, thereby developing a gene expression profile that differentiates a melanoma having the propensity to become virulent or aggressive and a melanoma not having said propensity.

* * * * *